(12) United States Patent
Biedermann et al.

(10) Patent No.: US 10,070,896 B2
(45) Date of Patent: Sep. 11, 2018

(54) ANCHORING MEMBER SUITABLE FOR USE IN A POLYAXIAL BONE ANCHORING DEVICE AND POLYAXIAL BONE ANCHORING DEVICE WITH AN ENLARGED PIVOT ANGLE TO ONE SIDE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 53 days.

(21) Appl. No.: 15/389,220

(22) Filed: Dec. 22, 2016

(65) Prior Publication Data

US 2017/0231665 A1    Aug. 17, 2017

Related U.S. Application Data

(63) Continuation of application No. 14/099,625, filed on Dec. 6, 2013, now Pat. No. 9,750,543.

(Continued)

(30) Foreign Application Priority Data

Dec. 10, 2012 (EP) .................................... 12196376

(51) Int. Cl.
*A61B 17/70* (2006.01)
*A61B 17/88* (2006.01)
(Continued)

(52) U.S. Cl.
CPC ...... *A61B 17/7037* (2013.01); *A61B 17/7082* (2013.01); *A61B 17/8615* (2013.01);
(Continued)

(58) Field of Classification Search
CPC ............. A61B 17/7038; A61B 17/7035; F16B 23/0046; F16B 23/0007–23/003
See application file for complete search history.

(56) References Cited

U.S. PATENT DOCUMENTS

| 5,545,228 A | 8/1996 | Kambin |
| 6,736,820 B2 | 5/2004 | Biedermann et al. |

(Continued)

FOREIGN PATENT DOCUMENTS

| JP | 11-019881 A | 1/1999 |
| JP | 2001340348 A | 12/2001 |

OTHER PUBLICATIONS

Office action for U.S. Appl. No. 14/099,625, dated Aug. 27, 2014, 12 pages.

(Continued)

*Primary Examiner* — Jacqueline Johanas
(74) *Attorney, Agent, or Firm* — Lewis Roca Rothgerber Christie LLP

(57) ABSTRACT

An anchoring member is provided suitable for use in a polyaxial bone anchoring device, the anchoring member (1) comprising
a bone anchoring section (2) with a bone engagement structure in at least a portion of an outer surface thereof;
a head (3);
a central axis (C) extending through a center of the head (3) and the bone anchoring section (2), and
a neck portion (24; 24'; 24"; 24''') between the bone anchoring section and the head, wherein the neck portion is asymmetric with respect to the central axis (C); and
wherein the bone anchoring section (2) has a contour in a circumferential direction adjacent to the neck portion and wherein the neck portion is at least partially recessed with respect to the contour of the bone anchor- (Continued)

ing section at one side and extends beyond the contour of the bone anchoring section at an opposite side from the central axis.

25 Claims, 6 Drawing Sheets

Related U.S. Application Data

(60) Provisional application No. 61/735,307, filed on Dec. 10, 2012.

(51) Int. Cl.
*A61B 17/86* (2006.01)
*A61B 17/00* (2006.01)
*A61B 17/56* (2006.01)

(52) U.S. Cl.
CPC .............. *A61B 2017/00455* (2013.01); *A61B 2017/564* (2013.01)

(56) References Cited

U.S. PATENT DOCUMENTS

| | | | |
|---|---|---|---|
| 7,485,132 B1 | 2/2009 | McBride et al. | |
| D642,270 S | 7/2011 | McAfee | |
| 8,029,539 B2 | 10/2011 | Kirschman | |
| 8,529,611 B2* | 9/2013 | Champagne | A61B 17/7225 606/301 |
| 9,216,039 B2* | 12/2015 | Jackson | A61B 17/861 |
| 2002/0058942 A1 | 5/2002 | Biedermann et al. | |
| 2003/0171755 A1 | 9/2003 | Moseley et al. | |
| 2004/0153077 A1* | 8/2004 | Biedermann | A61B 17/7032 606/305 |
| 2005/0015097 A1 | 1/2005 | Mujwid et al. | |
| 2005/0043735 A1 | 2/2005 | Ahmad | |
| 2006/0084995 A1* | 4/2006 | Biedermann | A61B 17/7032 606/279 |
| 2006/0106383 A1* | 5/2006 | Biedermann | A61B 17/7032 606/301 |
| 2009/0163961 A1* | 6/2009 | Kirschman | A61B 17/7032 606/301 |
| 2010/0160977 A1 | 6/2010 | Gephart et al. | |
| 2010/0204735 A1* | 8/2010 | Gephart | A61B 17/7037 606/264 |
| 2010/0312280 A1 | 12/2010 | Overes et al. | |
| 2011/0066189 A2* | 3/2011 | Biedermann | A61B 17/7032 606/301 |
| 2011/0125195 A1* | 5/2011 | Biedermann | A61B 17/7032 606/305 |
| 2011/0125265 A1 | 5/2011 | Bagga et al. | |
| 2011/0172719 A1 | 7/2011 | Gorhan et al. | |
| 2011/0276099 A1* | 11/2011 | Champagne | A61B 17/7225 606/328 |
| 2013/0281995 A1 | 10/2013 | Saunders et al. | |
| 2013/0325077 A1* | 12/2013 | Champagne | A61B 17/7225 606/328 |
| 2014/0148853 A1 | 5/2014 | Smith | |
| 2014/0188174 A1* | 7/2014 | Biedermann | A61B 17/7035 606/278 |
| 2014/0222079 A1* | 8/2014 | Matthis | A61B 17/7032 606/267 |

OTHER PUBLICATIONS

Final Office action for U.S. Appl. No. 14/099,625, dated May 12, 2015, 20 pages.
Office action for U.S. Appl. No. 14/099,625, dated Nov. 6, 2015, 20 pages.
Final Office action for U.S. Appl. No. 14/099,625, dated May 31, 2016, 21 pages.
Japanese Office action for Application No. 2013-251838, dated Oct. 25, 2016, including English translation, 12 pages.
Extended European Search Report for European Application No. 12196376.3, European Search Report dated May 22, 2013 and dated May 31, 2013 (10 pages).
Partial European Search Report for European Application No. 12196376.3, European Search Report dated Apr. 9, 2013 and dated Apr. 17, 2013 (5 pages).

\* cited by examiner

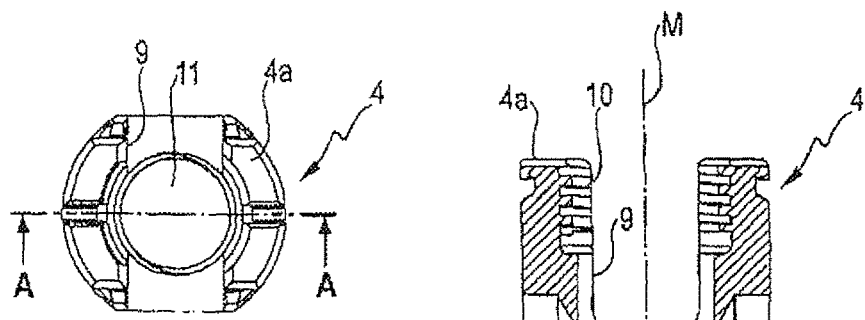
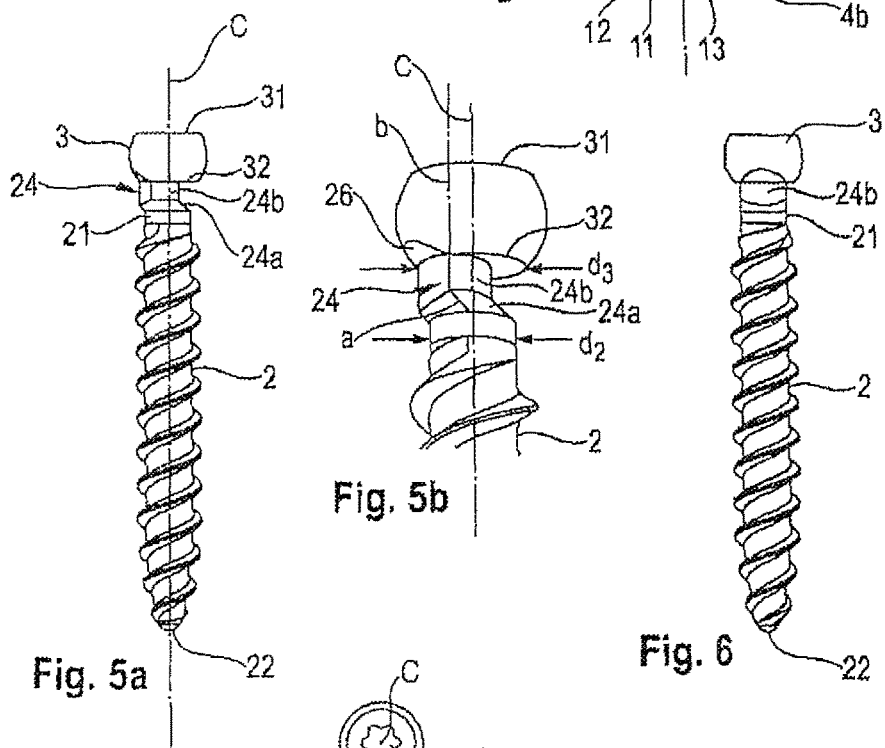

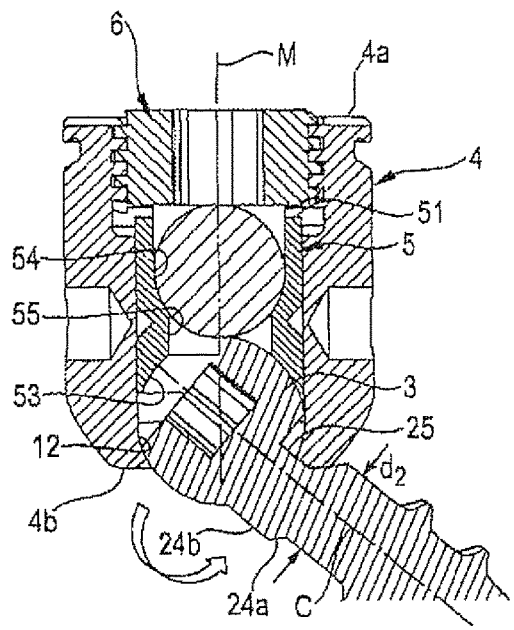
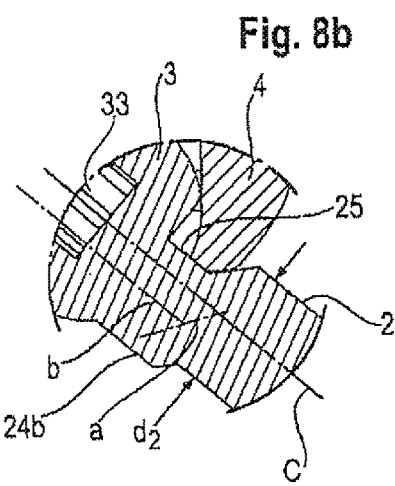
Fig. 8a
Fig. 8b
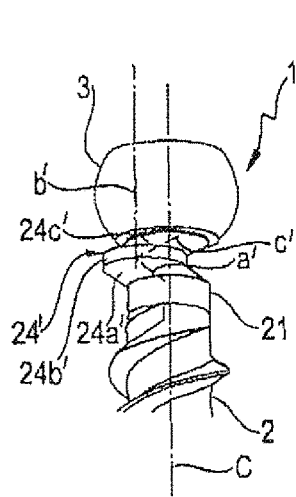
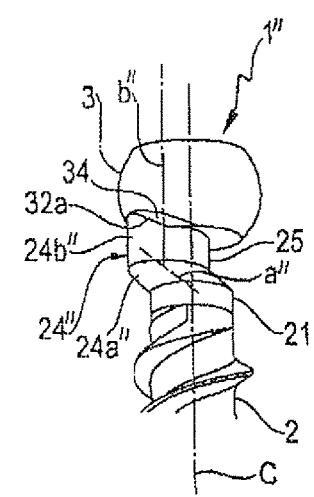
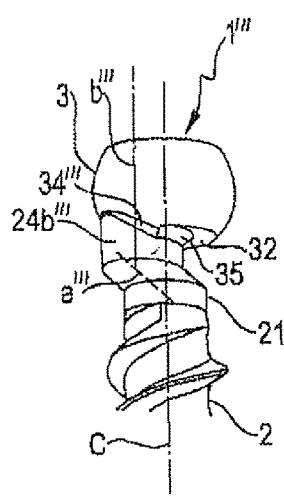
Fig. 9   Fig. 10   Fig. 11

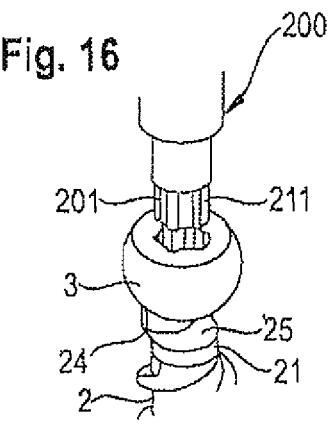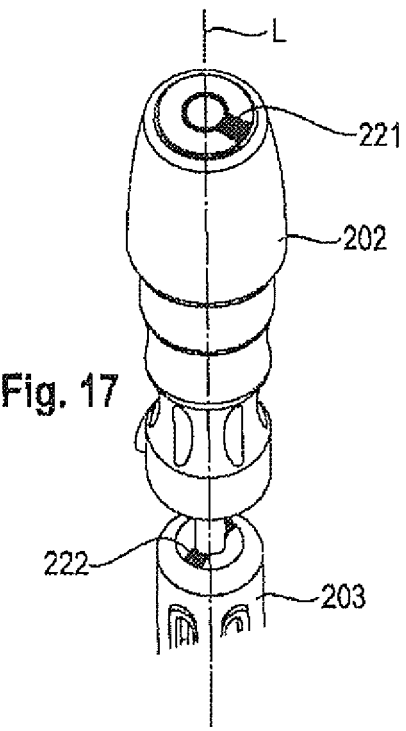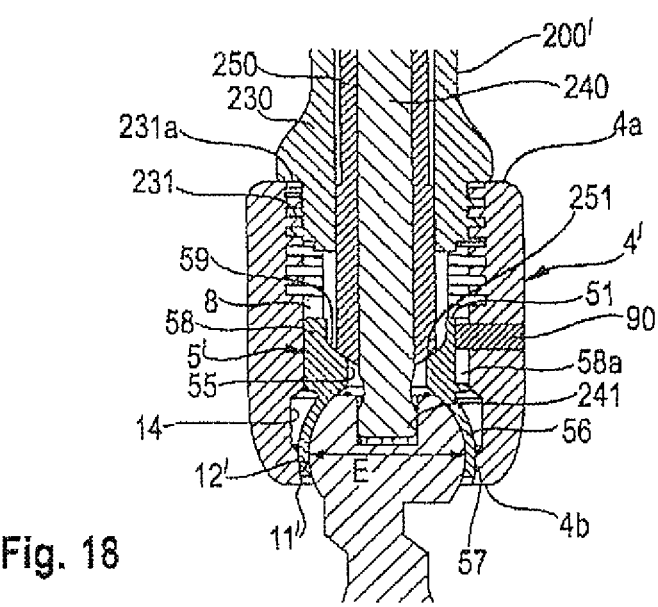

ANCHORING MEMBER SUITABLE FOR USE IN A POLYAXIAL BONE ANCHORING DEVICE AND POLYAXIAL BONE ANCHORING DEVICE WITH AN ENLARGED PIVOT ANGLE TO ONE SIDE

CROSS-REFERENCE TO RELATED APPLICATION(S)

This application is a continuation of U.S. patent application Ser. No. 14/099,625, filed Dec. 6, 2013, which claims priority to and the benefit of U.S. Provisional Patent Application Ser. No. 61/735,307, filed Dec. 10, 2012, the contents of which are hereby incorporated by reference in their entirety, and claims priority from European Patent Application EP 12 196 376.3, filed Dec. 10, 2012, the contents of which are hereby incorporated by reference in their entirety.

BACKGROUND

Field

The invention relates to an anchoring member suitable for use in a polyaxial bone anchoring device and to a polyaxial bone anchoring device with a pivot angle that is enlarged to one side. The anchoring member comprises a bone anchoring section and a head with a common central axis and a neck portion between the bone anchoring section and the head, wherein the neck portion is asymmetric with respect to the central axis. The asymmetry of the neck portion is established by a recess that is present at one side of the neck portion and an extension or projecting portion that is present at the opposite side of the neck portion. A polyaxial bone anchoring device including such an anchoring member permits pivoting of the anchoring member to at least one side with an enlarged pivot angle.

Description of Related Art

A bone anchoring device with an enlarged pivot angle to one side is described in U.S. Pat. No. 6,736,820. The bone anchoring device comprises a bone screw and a receiving part with an open first bore and a substantially U-shaped cross-section for receiving the rod and a second bore on the end opposite to the first bore and a seat for the head. In one embodiment, the screw member has a neck between a head and a threaded section, the neck having a recess or countersink and being asymmetric with respect to the symmetry axis. As a result thereof, the screw member can pivot at a larger angle to the side where the recess or countersink is present.

Another bone anchoring device with increased angulation is known from U.S. Pat. No. 8,029,539 B2. It includes a screw having a head, a shank and an intermediate or neck portion. The neck portion comprises a first surface or area having a relatively large radius and a second surface or area that has a relatively small radius. The larger and smaller radiuses of the surfaces permit the retainer of the anchoring device to be pivoted at a plurality of different angles or degrees.

SUMMARY

It is the object of the invention to provide an improved anchoring member suitable for use in a polyaxial bone anchoring device with an enlarged pivot angle to one side and a polyaxial bone anchoring device that has an increased strength with respect to loads acting on it. Furthermore, an instrument for use with the polyaxial bone anchoring device shall be provided.

The object is solved by a bone anchoring member according to claim 1, by a polyaxial bone anchoring device according to claim 14 and by an instrument according to claim 16. Further developments of the invention are given in the dependent claims.

The neck portion of the bone anchoring member is offset from a central axis extending through the head and the shank. Therefore, a polyaxial bone anchoring device including a receiving part and the bone anchoring member permits to pivot the bone anchoring member relative to the receiving part in a first direction at a first angle and in a second direction at a second angle wherein the second angle is greater than the first angle. The enlarged pivot angle may be as much as 55° measured from the central axis. An engagement portion for an instrument is provided on the head and the drive axis is coaxial with the central axis.

The bone anchoring member can be used with any known receiving part that is configured to pivotably receive a bone anchoring member. Hence, existing polyaxial bone anchoring devices can be modified into polyaxial bone anchoring devices with an enlarged pivot angle to one side by only exchanging the anchoring members. This contributes to a reduction of costs.

Because an overall thickness of the neck portion of the bone anchoring member is not reduced substantially, the strength and safety of the polyaxial bone anchoring device under loads is not diminished compared to a polyaxial bone anchoring device with a reduced thickness of the neck portion.

An alignment feature may be provided on the bone anchoring member that allows to pre-align the bone anchoring member relative to the receiving part with respect to the orientation of the enlarged pivot angle.

An instrument adapted to be used with the polyaxial bone anchoring device permits to indicate the orientation of the enlarged pivot angle relative to the receiving part even if the anchoring member is already inserted into the bone.

BRIEF DESCRIPTION OF DRAWINGS

Further features and advantages will be become apparent from the description of embodiment by means of the accompanying drawings. In drawings:

FIG. 3 shows a top view of the receiving part of the polyaxial bone anchoring device according to the first embodiment;

FIG. 4 shows a cross-sectional view of the receiving part, the cross-section taken along line A-A in FIG. 3;

FIG. 5a shows a side view of the bone anchoring member according to the first embodiment;

FIG. 5b shows an enlarged view of an upper portion of the bone anchoring member of FIG. 5a;

FIG. 6 shows a side view of the bone anchoring member of FIG. 5a, rotated by 90°;

FIG. 7 shows a top view of the bone anchoring member of FIG. 5a;

FIG. 8a shows a cross-sectional view of the polyaxial bone anchoring device according to the first embodiment, the cross-section taken along line A-A of the receiving part shown in FIG. 3;

FIG. 8b shows an enlarged view of a lower right portion of FIG. 8a;

FIG. 9 shows an enlarged perspective view of an upper portion of a bone anchoring member according to a second embodiment;

FIG. 10 shows an enlarged perspective view of an upper portion of a bone anchoring member according to a third embodiment;

FIG. 11 shows an enlarged perspective view of an upper portion of a bone anchoring member according to a fourth embodiment;

FIG. 16 shows an enlarged perspective view of a portion of the bone anchoring member with a front portion of an instrument for aligning the bone anchoring member with respect to the receiving part according to a first embodiment;

FIG. 17 shows a perspective view of a rearward portion of the instrument shown in FIG. 16;

FIG. 18 shows a cross-sectional view of a modified polyaxial bone anchoring device with a front portion of a second embodiment of an instrument;

DETAILED DESCRIPTION

Figure 1:
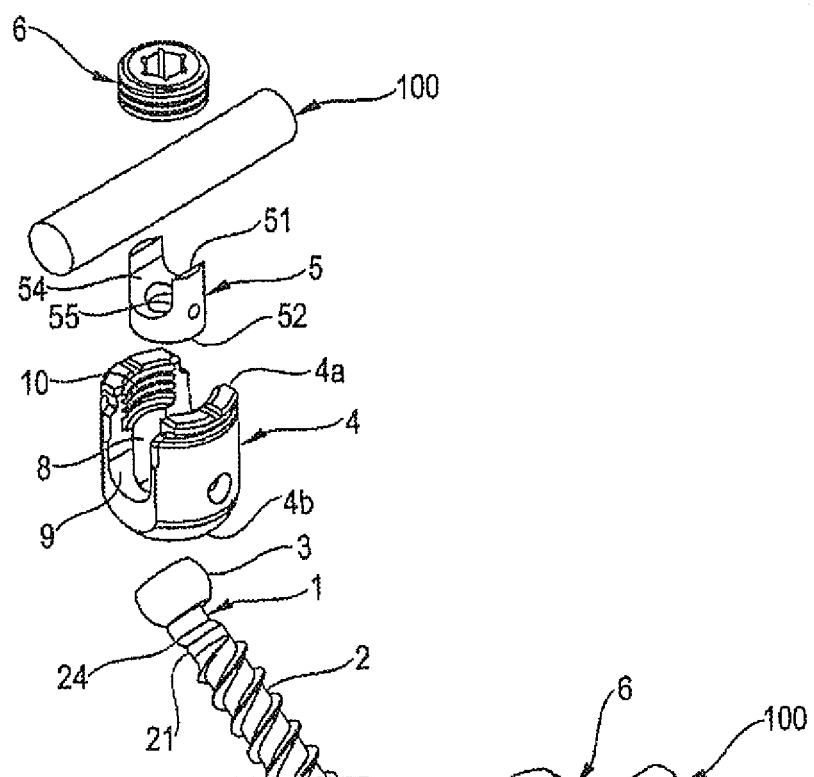
FIG. 1 shows an exploded perspective view of the polyaxial bone anchoring device according to a first embodiment.
Figure 2:
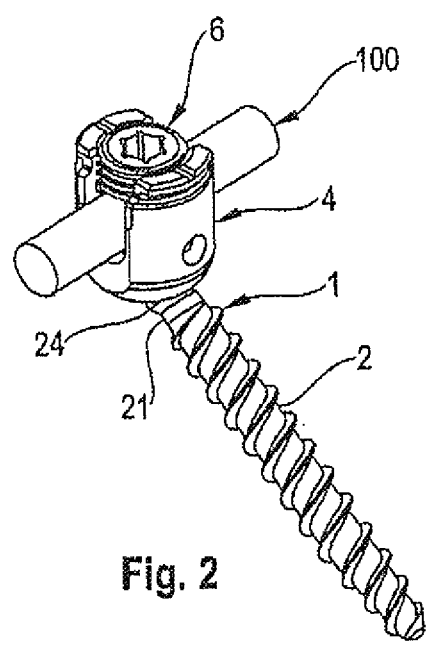
FIG. 2 shows a perspective view of the polyaxial bone anchoring device of FIG. 1 in an assembled state.

Referring to FIGS. 1 and 2, a polyaxial bone anchoring device according to a first embodiment includes a bone anchoring member 1 comprising a shank 2 for anchoring in a bone or a vertebra and a head 3. Further, a receiving part 4 for pivotably receiving the head 3 of the bone anchoring member 1 is provided that is configured to couple the bone anchoring member 1 to a stabilization rod 100. A pressure member 5 may be provided to exert pressure onto the head 3 in the receiving part 4 to lock the head 3 in a specific angular position with respect to the receiving part 4. Furthermore, a locking member 6 in the form of a set screw may be provided for securing and fixing the rod 100 in the receiving part 4.

Referring more in detail to FIGS. 3 and 4, the receiving part 4 has a top end 4a and a bottom end 4b, an axis of symmetry M and a coaxial bore 8 extending from the top end 4a in the direction of the bottom end 4b. Adjacent to the top end 4a, a substantially U-shaped recess 9 is provided that serves as a channel for receiving the rod 100. By means of the recess 9, two free legs are formed which are provided with an internal thread 10 for cooperating with the locking member 6.

The passage provided by the coaxial bore 8 narrows towards the second end 4b and an opening 11 is provided whose inner diameter is of such a size that the bone anchoring member can be guided through with its shank 2 until the head 3 is seated in a seat portion 12 adjacent to the opening 11. A portion 13 of a thread, for example, one turn of a thread may be provided in the seat portion 12 that permits the shank 2 to be screwed through the seat portion. This allows to use relatively large bone anchoring members without the necessity to increase the dimension of the seat and of the lower opening too much.

Referring now to FIGS. 5a to 7, the bone anchoring member 1 comprises a central axis C extending through the head 3 and the shank 2. The head 3 is substantially spherical segment-shaped and comprises a free end surface 31 and a bottom surface 32 opposite to the free end surface 31. At the free end surface 31, an engagement portion for an instrument in the form of a recess 33 is provided. A maximum diameter $d_3$ of the bottom surface 32 of the head 3 is smaller than a corresponding maximum diameter of the free end surface 31.

The shank 2 comprises first end 21 facing the head 3 and an opposite second end 22 that may be shaped as a tip. On at least a portion of the outer surface of the shank 2, a bone engagement structure in the form of a bone thread is provided. In a region adjacent to the first end 21, the shank has a maximum outer diameter $d_2$ and is symmetrical around the central axis C. The outer diameter $d_2$ may be the same as the core diameter of the bone thread. Between the first end 21 of the shank 2 and the bottom surface 32 of the head 3, a neck portion 24 is provided that connects the shank 2 to the head 3. The neck portion 24 is asymmetric with respect to the central axis, meaning that a central axis going through at least one section of the neck portion 24 does not coincide with the central axis C through the head 3 and the shank 2. More in detail, in the first embodiment, the neck portion 24 comprises a first inclined section 24a having substantially the same outer diameter as the outer diameter $d_2$ of the end portion 21 of the shank. A central axis a of the first section 24a extends at an angle with respect to the central axis C. Between the first section 24a and the bottom surface 32 of the head 3 is a second upright section 24b that has a central axis b extending substantially parallel to the central axis C. As can be seen in particular in FIG. 8b, the first inclined section 24a is shorter than the second upright section 24b. Hence, the first inclined section 24a serves for providing the second upright section 24b at a position offset from the central axis C.

Referring to FIGS. 8a and 8b, the offset of the central axis b of the second upright portion 24b provides a recessed area 25 between the bottom surface 32 of the head 3 and the first end 21 of the shank 2 that permits larger angulation in the direction of the recessed area as explained below.

Opposite to the recessed area 25, the second upright section 24b has an extension in radial direction that goes beyond the outer diameter $d_2$ of the end portion 21 of the shank 2 (see FIGS. 8a and 8b). Therefore, a total thickness in a radial direction of the second upright neck portion 24b is not substantially reduced compared to a neck portion that has only a recess or a countersink. The whole neck portion 24 may be manufactured by providing a cylindrical neck portion between the head 3 and the shank 2 that has a greater outer diameter compared to the end portion 21 of the shank 2 and removing a portion thereof at one side.

The pressure member 5 will be described referring to FIGS. 1 and 8a. The pressure member 5 is formed as a monolithic piece. It is of substantially cylindrical construction and has an outer diameter that allows it to move in the axial direction within the bore 8 of the receiving part 4. The pressure member 5 comprises a top end 51 and a bottom end 52. At the bottom end 52 the substantially spherical recess 53 is provided that is, adapted to the size of the head 3. At the top end 51, a substantially U-shaped recess 54 is formed that is configured to receive the rod 100 therein. In this embodiment, the surface of the rod extends above the side walls of the recess when the rod is inserted into the recess. More in detail, it may be advantageous if the side walls of the recess 54 extend to a height slightly below a height corresponding to the diameter of the rod when the rod is inserted. Furthermore, the pressure member 5 comprises a coaxial bore 55 for allowing access to the head 3 of the anchoring member with an instrument (not shown).

The locking member 6 is comprised of a set screw that can be screwed between legs of the receiving part 4. It is configured to contact the rod 100 when the rod 100 is inserted into the receiving part.

The parts of the polyaxial bone anchoring device are preferably made from a biocompatible material, in particular from a biocompatible metal or a metal alloy, such as titanium, stainless steel, Ni—Ti alloys such as Nitinol or from a biocompatible plastic material, such as, for example, polyether ether ketone (PEEK). The parts may be all of the same or of different materials.

The polyaxial bone anchoring device may be pre-assembled with the bone anchoring member 1 being inserted from the top end 4a into the receiving part until its head 3 presses in the seat 12. When the shank 2 is passed through the lower opening 11, the bone thread engages the portion 13 of a thread turn, so that the shank 2 can be screwed through the lower opening 11. The pressure member 5 may be rotationally fixed within the receiving part, for example, by crimping. In the pre-assembled state, the pressure member may exert a pre-load onto the head to preliminarily hold the head in a specific angular position by friction.

In use, at least two bone anchoring members 1 with receiving parts 4 are inserted into the bone or in adjacent vertebrae and connected through the rod 100. Referring in particular to FIGS. 8a and 8b, the bone anchoring member is permitted to pivot due to its recessed area 25 at the neck portion 24 at an angle to the right side that is greater than an angle to the left side with respect to the axis of symmetry M of the receiving part.

A second embodiment of the bone anchoring member is shown in FIG. 9. The bone anchoring member 1' comprises a neck portion 24' that is different from the neck portion 24 of the bone anchoring member of the previous embodiment. The neck portion 24' comprises a first section 24a', a central axis a' of which is angled with respect to the central axis C of the bone anchoring member 1', followed by a second section 24b' that is substantially cylindrical and a central axis b' of which is parallel to the central axis C of the bone anchoring member 1', further followed by a third section 24c' with a central axis c' that is angled with respect to the central axis C in an opposite direction compared to the central axis a'. The second portion 24b' extends beyond the end portion 21 of the shank 2 at one side. An area of the neck portion 24' of the cross-section in any plane perpendicular to the central axis C of the bone anchoring member 1' is substantially the same. In particular, an outer diameter of the second section 24b' is substantially the same as the outer diameter $d_2$ of the end portion 21 of the shank 2. Therefore, the strength of the neck portion 24' which has the offset section 24b' is substantially the same as that of a neck portion coaxial to the central axis C that has a diameter corresponding to that of the end portion 21 of the shank 2.

A third embodiment of the bone anchoring member is shown in FIG. 10. The bone anchoring member 1" comprises a neck portion 24" that has a first cylindrical inclined section 24a" with a central axis a" extending at an angle to the central axis C and a second upright cylindrical section 24b" with a central axis b" extending parallel to the central axis C. Hence, the second section 24b" extends beyond the end portion 21 of the neck 2 at one side and the neck portion 24" has a recessed area 25 on the opposite side. The second upright section 24b" goes over into the head 3 with a slanted surface 32a that provides enhanced stability. Also in this embodiment, an area of cross section in any plane perpendicular to the central axis C is substantially the same. In addition, the bone anchoring member 1" according to this embodiment may comprise slanted transition portions 34 between head 3 and the second section 24b" of the neck portion 24" to facilitate pivoting of the head 3 in the receiving part 4.

A fourth embodiment of the bone anchoring member is shown in FIG. 11. The bone anchoring member 1'" differs from the bone anchoring member 1" in that the slanted transition portions 34'" are narrower. In addition, a substantially rounded cutout portion 35 is provided at the transition between the second neck section 24b'" and the bottom side 32 of the head 3. Hence, the pivoting movement of the head 3 in the seat 12 of the receiving part 4 is further facilitated. The rounded cutout portion 35 may further increase the strength of the bone anchoring element under load due to the avoidance of an edge at the connection between the neck portion 24 and the head 3.

Figure 12:
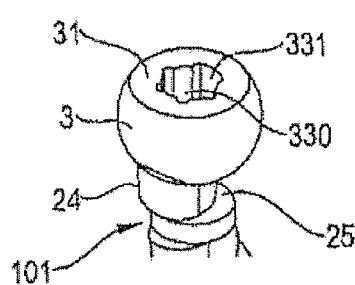
FIG. 12 shows a perspective view from the top of an upper portion of a modified bone anchoring member that has the alignment feature.

A further modified first embodiment of the bone anchoring member is shown in FIG. 12. The bone anchoring member 101 is identical to the bone anchoring member 1 according to the first embodiment except the design of the instrument engagement portion at the free end 31 of the head 3. The bone anchoring member 101 comprises an engagement portion 330 for an instrument at the free end surface 31 of the head 3 wherein the engagement portion 330 comprises an alignment feature 331 that is located at a position corresponding to the recessed region 25 between the shank 2 and the head 3 to indicate the position of the enlarged pivot angle. The alignment feature 331 is comprised of an enlarged portion of a torx-shaped recess at one side. It shall be noted, that the modified recess 330 can be used also in the embodiments shown in FIGS. 9 to 11.

Figure 13:
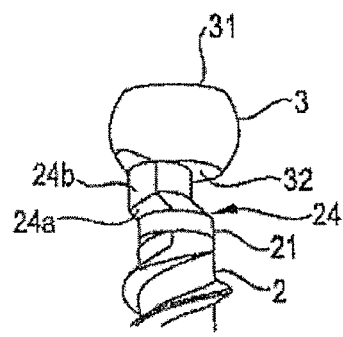
FIG. 13 shows a perspective view of an upper portion of the bone anchoring member according to the first embodiment with a further example of the alignment feature.

Referring to FIG. 13, an alignment feature can also be realized through the shape of the neck portion 24 itself. Because the bone anchoring member extends with at least a portion the neck portion through the lower opening 11, the shape of the neck portion with the offset section 24b provides an alignment feature to allow the alignment of the enlarged pivot angle.

Figure 14:
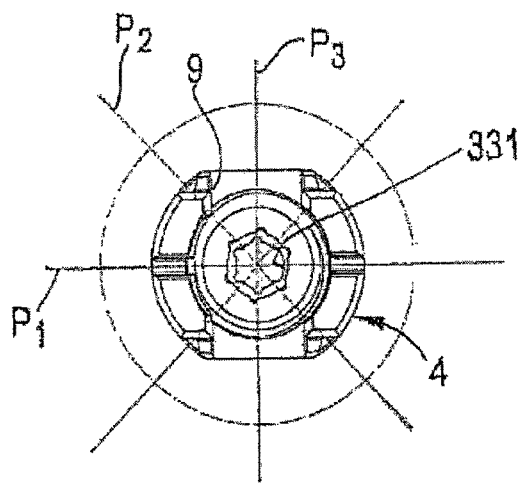
FIG. 14 shows a top view of a pre-assembled polyaxial bone anchoring device according to the first embodiment with the bone anchoring member pre-aligned.
Figure 15:
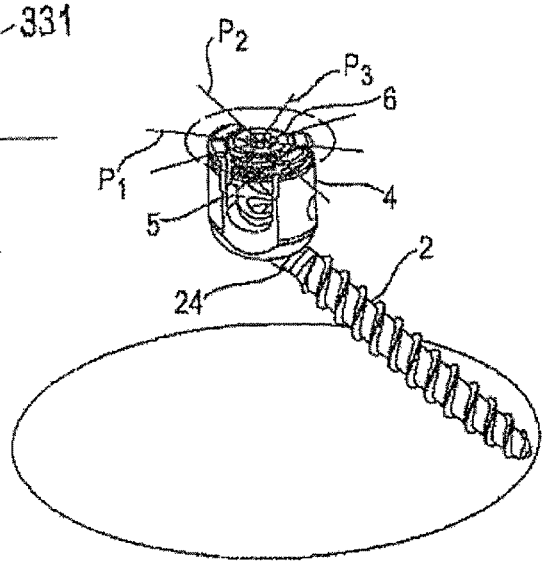
FIG. 15 shows a perspective view of the bone anchoring device of FIG. 14, after the bone anchoring member has been pivoted relative to the receiving part.

In a first method of use, the bone anchoring device is delivered in a pre-assembled form wherein the shank 2 is aligned in a pre-defined plane $p_1$ out of a plurality of planes $p_2, p_3 \ldots$ that contain the central axis M of the receiving part. As shown in FIG. 14, by means of the alignment feature 331 of the instrument engagement recess 330, the enlarged pivot angle is in the plane $p_1$ that extends perpendicular to the rod receiving recess 9. This plane may be pre-fixed by means of the locking member 6 pressing onto the pressure member 5 thereby lacking the head 3 in the receiving part 4. For that purpose, it may be advantageous if the side walls of the pressure member extend higher so that they can be engaged by the locking element 6. The surgeon may then insert the bone anchoring device into the bone. The pre-defined orientation of the plane that includes the enlarged pivot angle can be maintained by the friction force exerted onto the head via the pre-fixed pressure member.

Alternatively, a pre-alignment can be achieved by rotating the bone anchoring member so that by means of the shape of the neck the plane containing the enlarged pivot angle can be selected. With of both methods, pre-assembled, pre-aligned polyaxial bone anchoring devices can be delivered.

Referring to FIGS. 16 and 17, a first embodiment of an instrument 200 for inserting the bone anchoring member 1 comprises a drive portion with a longitudinal axis L. The drive portion includes a front portion 201 that is configured to engage the recess 330. To achieve this, the front portion 201 comprises a torx-shape with a broadened section 211 that fits into the portion 331 of the recess 330. An end portion 202 opposite to the front portion 201 of the instrument comprises a handle and an indication mark 221 at the free end surface of the handle that is visible for a user. The indication mark 221 may be coloured or engraved and may be a stripe or an engraved section that has an orientation corresponding to the location of the broadened section 211 of the front portion 201. Hence, when the front portion 201 engages the recess 330 the indication mark 221 indicates the position of the broadened portion 211 of the front portion and therefore also indicates a position of the recessed region 25 between the bottom side 32 of the head 3 and the shank 2. As a result, a user can see the orientation of the plane with the enlarged pivot angle by means of the position of the indication mark 221.

The instrument 200 may further include a holding portion 203 that can be connected to the receiving part 4. At an upper surface of the holding portion 203 an indication mark 222, such as a coloured stripe or an engraved portion is provided indicating the orientation of the rod 100. The drive portion is rotatable with respect to the holding portion 203. Thus, when screwing in the bone anchoring element with the drive portion, the indication mark 221 indicates the orientation of the recessed area 25 of the anchoring element 101 relative to the orientation of the rod that is indicated by the indication mark 222.

In a second method of use, the bone anchoring member 1 is screwed into a bone part or a vertebra using the instrument 200 that engages the recess 330. The indication mark 222 indicates the orientation of the rod. The indication mark 221 indicates the position of the bone anchoring member with respect to the receiving part and therefore the orientation of the enlarged pivot angle with respect to the rod.

FIG. 18 shows a second embodiment of a polyaxial bone anchoring device and a second embodiment of an instrument. The polyaxial bone anchoring device differs with respect to the receiving part and the pressure member. Parts and portions that have the same reference numerals will not be repeated. The receiving part 4' allows to insert the bone anchoring member 1 from the bottom end 4b. To achieve this, an opening 11' at the bottom end 4b is larger than a largest outer diameter of the head 3, so that the head 3 can be inserted to the opening 11'. Adjacent to the lower opening 11', there is a narrowing seat portion 12', that may be conically-shaped. Following the seat portion 12', there is an accommodation space 14 for accommodating the head 3 and a portion of the pressure member 5'. The pressure member 5' comprises a lower cap-like portion 56 that encompasses the head 3 from the free-end of the head 3 until a position below the equator E of the head 3, i.e. the portion with the largest diameter. The lower cap-like portion 56 may be flexible, for example by means of slits. The cap-like portion 56 comprises at its lower end an outer tapered section 57 that cooperates with the seat portion 12'. An upper portion 58 of the pressure member 5' is cylindrically shaped and comprises an outer diameter that permits to move within the bore 8. Preferably, at one side an elongate recess 58a is provided in the upper portion 58 of the pressure member 5' that can be engaged by a pin 90 extending through the wall of the receiving part into the recess and limiting an upward movement of the pressure member 5' in the direction of the top end 4a. The pressure member has a substantially V-shaped recess 59 adjacent to its top end 51 that opens into the coaxial bore 55 in the center of the pressure member 5' and permits to insert rods of different diameters.

The bone anchoring device according to the second embodiment is usually delivered as a pre-assembled device comprising the receiving part 4' and the pressure member 5'. It can be combined with the bone anchoring member 1, 1', 1", 1''' according to one of the previously described embodiments by inserting the head 3 through the lower opening until the cap-like lower portion 56 snaps onto the head 3. The head 3 can be locked by moving the pressure member 5' downwards until the tapered section of the seat portion 12' and the outer tapered section 57 of the lower cap-like portion 56 of the pressure member 5' engage and clamp the head. Before final locking of the head 3, the head 3 is pivotable in the lower cap-like portion 56 of the pressure member 5'.

An instrument 200' according to the second embodiment comprises an outer tube-like portion 230, comprising a front end 231 with an external thread cooperating with the internal thread 10 of the receiving part 4'. The front portion 231 comprises a surface 231a that abuts against the top end 4a of the receiving part 4' to limit the insertion of the outer tube-like portion 230.

The instrument 200' further comprises a central post 240 with a front end 241 comprising an engagement portion similar to the engagement portion 201 of the instrument 200, that has an asymmetry to fit into the recess 330 of the head of the bone anchoring member. At an opposite end 242 of the central post there is an indication mark 243 at a position corresponding to the alignment feature of the front portion 241 of the central post. The indication mark 243 indicates the position of the alignment feature at the front end 241. A tubular member 250 is provided around the central post 240 and inside the outer tube-like portion 230 of the instrument 200'. A front end 251 of the tubular member 250 abuts against the essentially V-shaped recess 59 of the pressure member 5'. An opposite end 252 of the tubular member 250 comprises a flat end surface with an indication mark 253 in the form of, for example a longitudinal stripe extending across the end surface 252. The indication mark 253 indicates a position of the rod receiving channel 59 in the pressure member 5' and the orientation of the U-shaped recess 9 in the receiving part 4'. The end surface 252 further comprises a central opening through which the end surface 242 of central post 240 can extend. Furthermore, a handle 232, connected to the outer tube-like portion 230 may be provided. The central post 240 and the outer tubular member 250 are rotateable with respect of the outer tube-like portion 230 of the instrument 200'.

Figure 19:
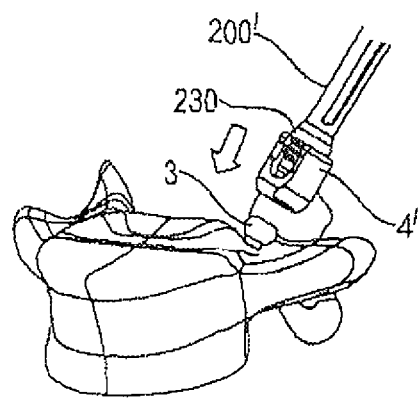
FIG. 19 shows a perspective view of a step of in-situ assembling the polyaxial bone anchoring device of FIG. 18 with the instrument.
Figure 20:
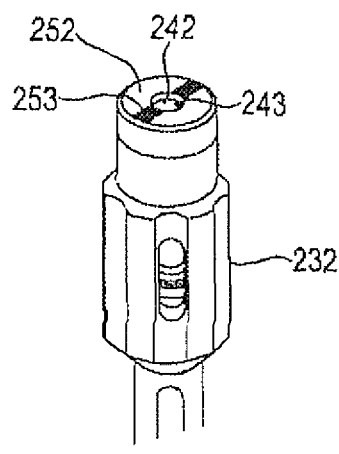
FIG. 20 shows a perspective view of an upper portion of the instrument shown in FIGS. 18 and 19 in a first configuration.
Figure 21:
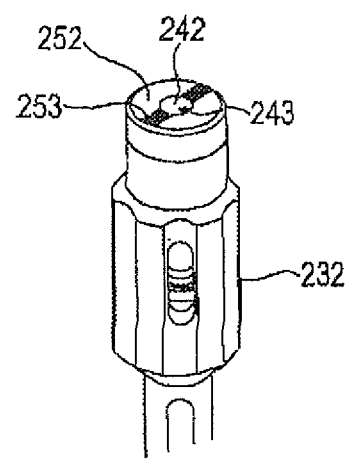
FIG. 21 shows a perspective view of an upper portion of the instrument in a second configuration.

In a third method of use, first, the bone anchoring member 1 is inserted into, for example, a pedicle of a vertebra as shown in FIG. 19. Then, the assembly consisting of the receiving part 4' with pre-assembled pressure member 5' is connected to the tool 200' by screwing the outer tubular portion 230 into the receiving part 4'. Thereafter, the assembly is connected to the head 3 of the bone anchoring member 1 by inserting the head 3 into the receiving part 4' and more particular into the lower cap-like portion 56. The outer tubular member 250 abuts against the recess 59 of the pressure member 5' when the pressure member 5' is correctly mounted. The indication mark 253 indicates the orientation of the rod to be inserted later. The indication mark 243 at the free end 242 of the central post 240 indicates the orientation of the enlarged pivot angle relative to the rod orientation. The dimension of the portions of the instrument 200' is such that the free-end surface 242 of the central post 240 is flush with the free-end surface 252 when the receiving part 4' is correctly placed onto the head 3. Therefore, with the two indication marks 243, 253, the orientation of the enlarged pivot angle with respect to the orientation of the rod 100 can be identified in the case of a polyaxial bone anchoring device of the bottom loading type.

Modifications of the above embodiments are possible. For the bone engagement structure of the shank 2, all kinds of bone engagement structures may be conceivable, such as barbs, a roughened surface, other kinds of bone threads etc. Cannulated screws may also be used. An end portion of the shank adjacent to the neck portion may have a non-circular cross-section, for example it may have a square or rectangular cross-section. The offset neck portion then extends beyond such a contour at a side opposite to the recessed area 25.

For the receiving part, all kinds of known receiving parts can be used that allow a pivoting of a bone anchoring member in a seat provided in the receiving part or in a pressure member. Such a receiving part can be configured to couple the bone anchoring member to a rod. Also, the receiving part can be provided in a bone plate.

A variety of known locking elements, including two part locking devices may be used.

The features of the different embodiments may also be combined among each other.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An anchoring member for a polyaxial bone anchoring device, the anchoring member comprising:
   a bone anchoring section having a first end, a second end, and a bone engagement structure on at least a portion thereof;
   a head, wherein a central axis extends through respective centers of the head and the first and second ends of the bone anchoring section; and
   a neck between the bone anchoring section and the head;
   wherein a first portion of the anchoring member is asymmetric with respect to the central axis;
   wherein an inner wall of the head defines a recess for an instrument, the recess having a plurality of points or vertices arranged equidistantly from one another for all 360 degrees around the central axis, and a plurality of inner wall portions respectively connecting adjacent pairs of the plurality of points or vertices, wherein each of the points or vertices defines a greatest distance between the central axis and the inner wall, and wherein a first inner wall portion is shaped differently from both respective inner wall portions that are adjacent to the first inner wall portion, such that the recess defines another asymmetric portion relative to the central axis to form an alignment feature for identifying an orientation of the asymmetric first portion relative to the central axis.

2. The anchoring member of claim 1, wherein the head is shaped as a spherical segment.

3. The anchoring member of claim 1, wherein the head comprises a flattened or rounded transition at a side facing the neck.

4. The anchoring member of claim 1, wherein the central axis is coaxial with a drive axis or axis of rotation of the anchoring member.

5. The anchoring member of claim 1, wherein the recess is at a free end surface of the head.

6. The anchoring member of claim 1, wherein the recess forms an asymmetric torx-shape, with an enlarged recessed portion formed by increasing a distance between the central axis and the first inner wall portion.

7. The anchoring member of claim 1, wherein the neck comprises the asymmetric first portion.

8. The anchoring member of claim 7, wherein the neck has at least one section with two ends and an axis extending through the two ends that is substantially parallel to the central axis.

9. The anchoring member of claim 7, wherein the neck has at least one section with two ends and an axis extending through the two ends that is at an angle relative to the central axis.

10. The anchoring member of claim 7, wherein the neck has two sections each having two ends and an axis extending through the two ends, wherein the respective axes of the two sections of the neck are at angles relative to the central axis.

11. The anchoring member of claim 10, wherein the angles of the respective axes of the two sections of the neck are oriented opposite to one another relative to the central axis, and wherein at least a portion of the neck adjacent to the head is aligned with the central axis.

12. The anchoring member of claim 7, wherein the bone engagement structure is a bone thread, and wherein at least some of the neck extends farther from the central axis than a root of the bone thread extends from the central axis.

13. The anchoring member of claim 7, wherein at least two cross-sectional areas of the neck that are perpendicular to the central axis are substantially the same as one another.

14. The anchoring member of claim 7, wherein at least a portion of the neck is recessed relative to other portions of the neck to form the asymmetry, and wherein the alignment feature identifies an orientation of the recessed portion of the neck.

15. The anchoring member of claim 7, wherein the alignment feature further comprises a shape of the neck.

16. The anchoring member of claim 7, wherein the bone anchoring section defines a contour in a circumferential direction at a region adjacent to the neck, and wherein at least part of the neck is recessed relative to the contour in a first radial direction and extends beyond the contour in a second radial direction.

17. A polyaxial bone anchoring device comprising:
   the anchoring member of claim 1; and
   a receiving part having an axis of symmetry and configured to pivotably receive the anchoring member;
   wherein the bone anchoring device is configured to pivot the anchoring member relative to the receiving part in a first radial direction at a first maximum angle, and to pivot the anchoring member relative to the receiving part in a second radial direction at a second maximum angle that is less than the first maximum angle.

18. The polyaxial bone anchoring device of claim 17, further comprising a pressure member configured to exert pressure on the head in the receiving part.

19. A system comprising:
   the anchoring member of claim 1; and an instrument for use with the anchoring member, wherein the instrument comprises a first portion with an asymmetric engagement portion configured to fit into the recess and a second portion with an indication mark for identifying an orientation of the asymmetric engagement portion.

20. A method for coupling a rod to a bone via a polyaxial bone anchoring device comprising a receiving part, a locking element, and an anchoring member configured to be pivotably connected to the receiving part, the anchoring member comprising a bone anchoring section having a first end, a second end, and a bone engagement structure on at least a portion thereof, a head, wherein a central axis extends through respective centers of the head and the first and second ends of the bone anchoring section, and a neck between the bone anchoring section and the head, wherein a first portion of the anchoring member is asymmetric with respect to the central axis, wherein an inner wall of the head defines a recess for an instrument, the recess having a plurality of points or vertices arranged equidistantly from one another for all 360 degrees around the central axis, and a plurality of inner wall portions respectively connecting adjacent pairs of the plurality of points or vertices, wherein each of the points or vertices defines a greatest distance between the central axis and the inner wall, and wherein a first inner wall portion is shaped differently from both respective inner wall portions that are adjacent to the first inner wall portion, such that the recess defines another asymmetric portion relative to the central axis to form an alignment feature for identifying an orientation of the asymmetric first portion relative to the central axis, the method comprising:
  inserting the anchoring member into a bone;
  adjusting an angular position of the receiving part relative to the anchoring member;
  inserting a rod into a channel of the receiving part; and
  advancing the locking element in the receiving part to lock the angular position of the anchoring member and a position of the rod relative to the receiving part.

21. The method of claim 20, further comprising adjusting a rotational position of the anchoring member relative to the bone to position the asymmetric first portion at a desired orientation.

22. The method of claim 20, further comprising engaging the instrument with the recess of the anchoring member to identify and/or adjust an orientation of the asymmetric first portion relative to the bone.

23. The method of claim 20, further comprising connecting the anchoring member and the receiving part.

24. An anchoring member for a polyaxial bone anchoring device, the anchoring member comprising:
  a bone anchoring section having a first end, a second end, and a bone engagement structure on at least a portion thereof;
  a head, wherein a central axis extends through respective centers of the head and the first and second ends of the bone anchoring section; and
  a neck between the bone anchoring section and the head;
  wherein a first portion of the anchoring member is asymmetric with respect to the central axis;
  wherein an inner wall of the head defines a recess for an instrument, the recess having a plurality of points or vertices arranged equidistantly from one another for all 360 degrees around the central axis, and a plurality of inner wall portions respectively connecting adjacent pairs of the plurality of points or vertices, wherein each of the points or vertices defines a greatest distance between the central axis and the inner wall, and each point or vertex is directly connected to at least one inner wall portion with a region that is positioned closer to the central axis than the greatest distance, and wherein the recess defines another asymmetric portion relative to the central axis to form an alignment feature for identifying an orientation of the asymmetric first portion relative to the central axis.

25. The anchoring member of claim 24, wherein the neck comprises the asymmetric first portion.

* * * * *

UNITED STATES PATENT AND TRADEMARK OFFICE
CERTIFICATE OF CORRECTION

PATENT NO. : 10,070,896 B2
APPLICATION NO. : 15/389220
DATED : September 11, 2018
INVENTOR(S) : Lutz Biedermann et al.

Page 1 of 1

It is certified that error appears in the above-identified patent and that said Letters Patent is hereby corrected as shown below:

In the Specification

Column 6, Line 60, delete "lacking" and insert -- locking --

Signed and Sealed this
Twenty-fourth Day of September, 2019

Andrei Iancu
*Director of the United States Patent and Trademark Office*